United States Patent [19]
Frank

[11] Patent Number: 5,511,689
[45] Date of Patent: Apr. 30, 1996

[54] DISPENSING DEVICE FOR ADHESIVE-BACKED ARTICLES

[76] Inventor: Richard D. Frank, 11909 S. Lake Dr., Houston, Tex. 77077

[21] Appl. No.: 422,078

[22] Filed: Apr. 20, 1995

Related U.S. Application Data

[63] Continuation of Ser. No. 173,978, Dec. 28, 1993, abandoned.

[51] Int. Cl.$^6$ .................................................. B65H 5/28
[52] U.S. Cl. ............................... 221/73; 221/71; 221/79; 221/25; 221/28; 221/49; 221/197; 206/440
[58] Field of Search ................................. 221/25, 28, 49, 221/70, 71, 73, 197, 309, 312 C, 72, 77, 79; 156/289, 344; 428/40, 41, 42; 206/440, 441, 820, 229

[56] References Cited

U.S. PATENT DOCUMENTS

| | | | |
|---|---|---|---|
| Re. 32,010 | 10/1985 | Collins | 156/527 |
| Re. 33,727 | 10/1991 | Sims | 128/85 |
| 2,465,876 | 3/1949 | Hornung | 206/16 |
| 2,587,928 | 3/1952 | Tuck et al. | 312/39 |
| 2,627,341 | 2/1953 | Morgan | 206/63.2 |
| 2,887,247 | 5/1959 | Williams | 221/25 |
| 3,313,405 | 4/1967 | Blackford | 206/63.2 |
| 3,520,403 | 7/1970 | Moshel | 206/63.2 |
| 3,530,494 | 9/1970 | Baratta | 206/63.2 |
| 3,630,346 | 12/1971 | Burnside | 206/56 AB |
| 3,809,221 | 5/1974 | Compere | 206/461 |
| 3,835,992 | 8/1974 | Adams | 206/390 |
| 3,899,077 | 8/1975 | Spiegelberg | 206/441 |
| 4,182,449 | 1/1980 | Kozlow | 206/441 |
| 4,194,624 | 3/1980 | Spiegelberg | 206/441 |
| 4,265,234 | 5/1981 | Schaar | 128/156 |

(List continued on next page.)

FOREIGN PATENT DOCUMENTS

| | | | |
|---|---|---|---|
| 0051935A2 | 5/1982 | European Pat. Off. | A61F 13/02 |
| 0066899A2 | 12/1982 | European Pat. Off. | A61F 13/02 |
| 0081990A1 | 5/1983 | European Pat. Off. | A61F 13/02 |
| 1002738 | 3/1952 | France . | |
| 59-214449 | 12/1984 | Japan | A61F 13/02 |
| 2120104A | 11/1983 | United Kingdom | A61F 13/02 |
| WO89/11262 | 11/1989 | WIPO | A61F 13/02 |

OTHER PUBLICATIONS

"Bertek Pouch/Patch Applicator Wound Dressing Machine," pp. 4, 6, 28, 46 and 62 (1991).

"Basic Applications for Tegaderm™ Transparent Dressings", Tegaderm™ Transparent Dressing, Suggested Applications and Special Techniques, 3M Health Care, pp. 2–17, Oct. 1991.

*Primary Examiner*—William E. Terrell
*Assistant Examiner*—Dean A. Reichard
*Attorney, Agent, or Firm*—Arnold, White & Durkee

[57] ABSTRACT

An apparatus is disclosed for dispensing an adhesive-backed article. An adhesive-backed article has a first adhesive disposed on at least a portion of its bottom surface. The bottom surface of the adhesive-backed article is bonded to the top surface of a backing layer by a bond formed by the first adhesive. The top surface of the adhesive-backed article is bonded to the bottom surface of the support layer by a bond formed by a second adhesive disposed on at least a portion of the bottom surface. The bond formed between the top surface of the adhesive backed article and the bottom surface of the support layer is stronger than the bond between the bottom surface of the adhesive-backed article and the top surface of the backing layer such that when the support layer is separated from the backing layer, .the adhesive-backed article remains affixed to the support layer. Further, the bond formed between the top surface of the adhesive-backed article and the bottom surface of the support layer is weaker than a bond formed between the adhesive on the bottom surface of the adhesive backed article and a surface to which it is applied, such that when the adhesive-backed article is applied to an application surface and the support layer separated from this surface, said adhesive-backed article will remain bonded to the application surface.

30 Claims, 2 Drawing Sheets

U.S. PATENT DOCUMENTS

| | | | |
|---|---|---|---|
| 4,336,097 | 6/1982 | Van Kampen et al. | 156/527 |
| 4,499,896 | 2/1985 | Heinecke | 128/156 |
| 4,600,001 | 7/1986 | Gilman | 128/156 |
| 4,666,040 | 5/1987 | Murata | 206/441 |
| 4,759,652 | 7/1988 | Ulrich | 401/196 |
| 4,787,380 | 11/1988 | Scott | 128/156 |
| 4,807,753 | 2/1989 | Goldstein | 206/390 |
| 4,915,102 | 4/1990 | Kwiatek et al. | 128/156 |
| 4,993,586 | 2/1991 | Taulbee et al. | 221/25 |
| 5,102,008 | 4/1992 | Kaufman et al. | 221/25 |
| 5,133,477 | 7/1992 | Etheredge et al. | 221/25 |
| 5,160,315 | 11/1992 | Heinecke | 602/57 |
| 5,242,725 | 9/1993 | Weissman et al. | 428/40 |

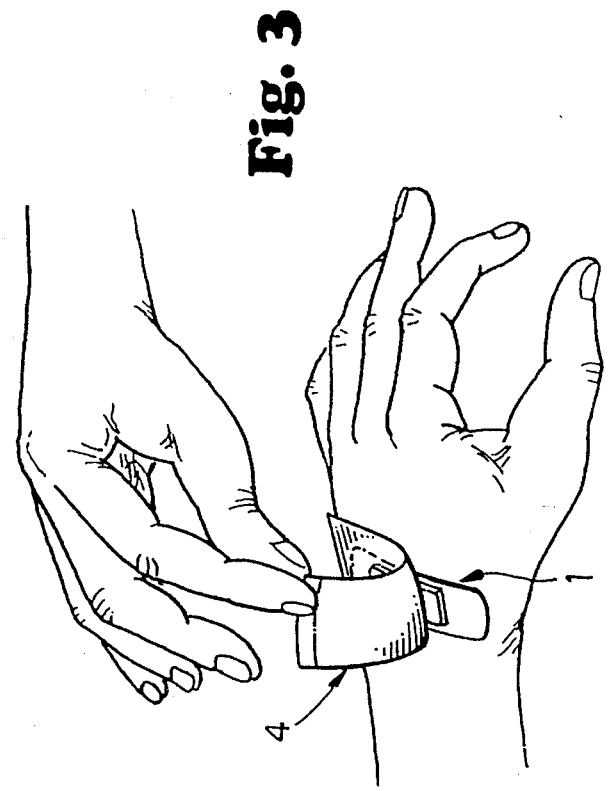
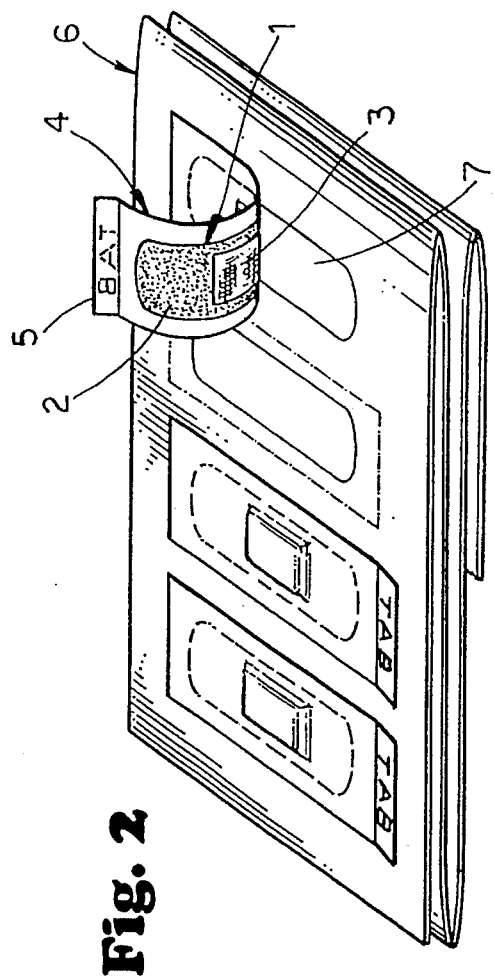
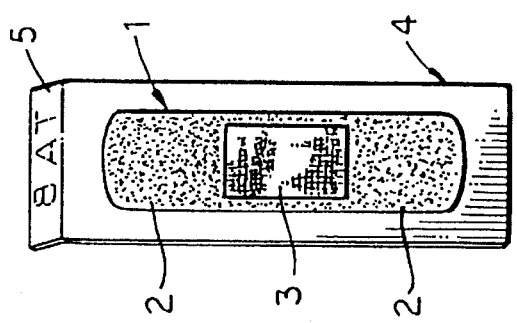

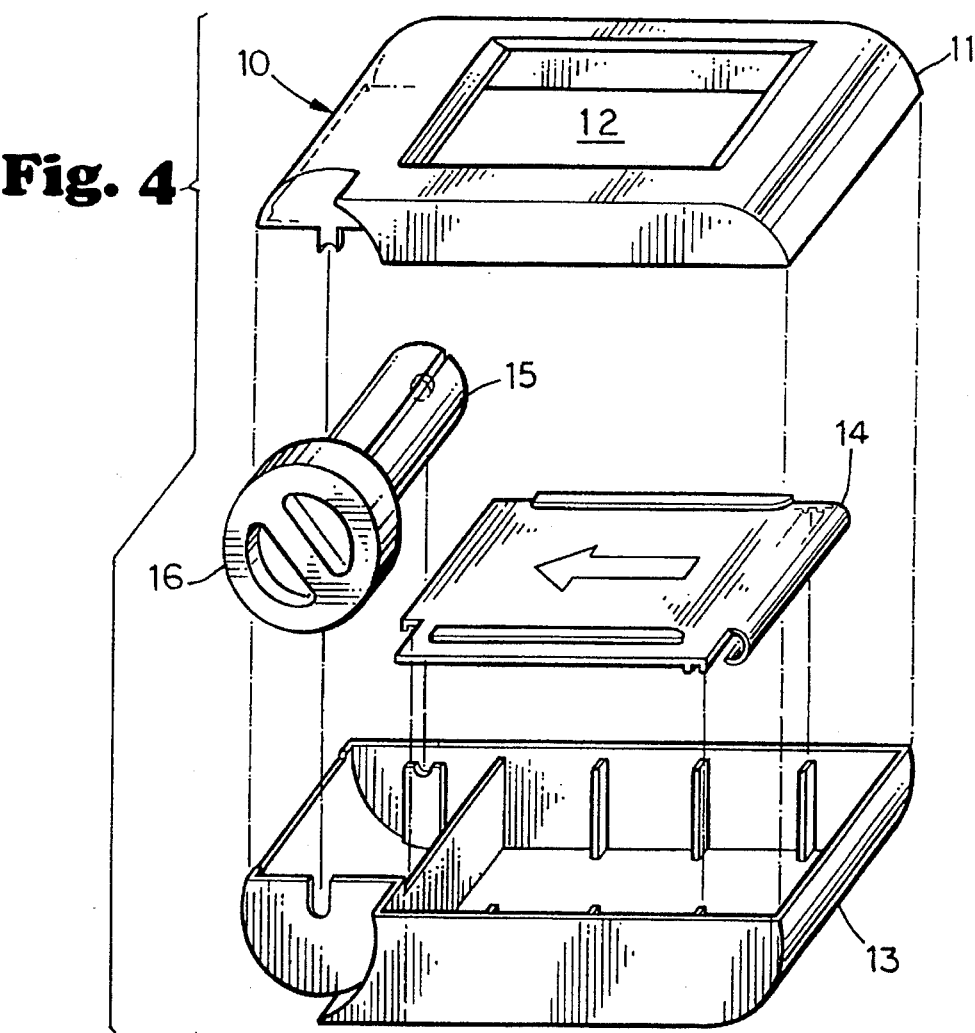
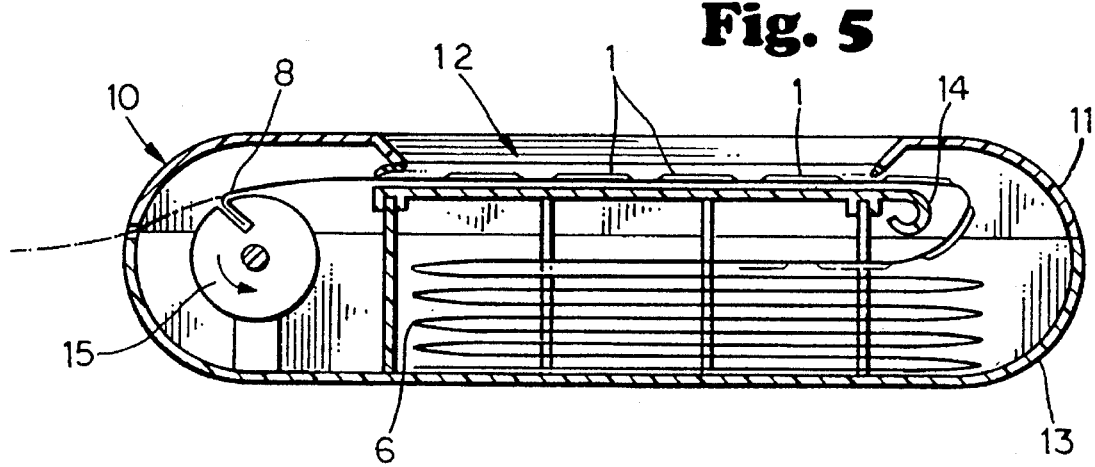

DISPENSING DEVICE FOR ADHESIVE-BACKED ARTICLES

This application is a continuation of currently pending application Ser. No. 08/173,978, filed Dec. 28, 1993, now abandoned.

TECHNICAL FIELD

This invention relates to a dispensing device for adhesive-backed articles, such as bandage strips. More particularly, this invention permits one-handed access, removal, and application of adhesive-backed articles.

BACKGROUND OF THE INVENTION

While adhesive-backed articles such as adhesive bandage strips are known in the art, they are commonly sealed in sterile, individual wrappings and packaged within paper or metal boxes. Examples include the well-known "Band-Aid®" brand bandage strips. While popular, these products suffer certain disadvantages such as the fact that the bandages themselves can be difficult to remove from the wrappings and difficult to apply to the desired location. The user generally must remove the bandage from the wrapping, remove the nonstick layers from the adhesive portion of the bandage and then attempt to apply the bandage to the desired location without the bandage curling or having the bandage adhere to itself.

Attempts to improve upon this concept include U.S. Pat. No. 4,993,586 to Taulbee, et al. which discloses a bandage dispenser device in which a continuous strip is grasped with one hand and a bandage is removed with the other hand. This is accomplished by the use of a continuous strip with a first and second layer. Bandages are placed on sterile mounting pads affixed to the first layer. The bandages and the first layer are then enclosed by a second layer and stacked or rolled within a container. In use, the sheet is pulled through a splicer attached to the container that cuts the first and second layer. The second layer is then lifted and removed. The first layer is then grasped with one hand and a bandage is removed with the other.

U.S. Pat. No. 5,133,477 to Etheredge, et al., also discloses a bandage dispenser device employing the use of a continuous strip. The strip has a nonstick coating upon which one end of a bandage is affixed. The other end of the bandage and the cotton gauze area of the bandage are covered with a release sheet. In use, the continuous sheet is grasped with one hand and the bandage is grasped and removed with the other hand. The bandage is then applied to the desired location by affixing the exposed half to the skin. Once applied, this end of the bandage is held in place while the release sheet is removed from the bandage and the other end of the bandage is applied to the skin.

Despite these and other prior art devices, there remains a need for a dispensing device for adhesive-backed articles, such as adhesive bandage strips, by which the article may be grasped with one hand from the front of a dispenser and then applied, also one-handedly, to the desired location without the article curling or adhering to itself. Both Taulbee and Etheredge require the use of two hands to remove and apply a bandage strip and neither address the problem of the bandage strip curling or adhering to itself. Further, the device disclosed by Taulbee would entail considerable manufacturing costs due to the splicer structure.

While the prior art has improved upon access to adhesive-backed articles, there is a need for both improved access to the article and improved applicability of the article. This would permit, for example, a lab technician who is drawing blood from a patient to apply an adhesive bandage strip with one hand while maintaining pressure on the puncture with the other.

SUMMARY OF THE INVENTION

Stated generally, the present invention comprises an apparatus for dispensing an adhesive-backed article. An adhesive-backed article has a first adhesive disposed on at least a portion of its bottom surface. The bottom surface of the adhesive-backed article is bonded to the top surface of a backing layer by a bond formed by the first adhesive. The top surface of the adhesive-backed article is bonded to the bottom surface of the support layer by a bond formed by a second adhesive disposed on at least a portion of the bottom surface. The bond formed between the top surface of the adhesive-backed article and the bottom surface of the support layer is stronger than the bond between the bottom surface of the adhesive-backed article and the top surface of the backing layer such that when the support layer is separated from the backing layer, the adhesive-backed article remains affixed to the support layer. Further, the bond formed between the top surface of the adhesive backed article and the bottom surface of the support layer is weaker than a bond formed between the adhesive on the bottom surface of the adhesive-backed article and a surface to which it is applied, such that when the adhesive-backed article is applied to an application surface and the support layer separated from said surface, said adhesive-backed article will remain bonded to said application surface.

Embodiments of this invention include the use of adhesive bandage strips positioned on a continuous sheet and packed within a dispenser. Sterile, nonstick mounting pads are affixed to the continuous sheet and the adhesive bandage strips are placed on each of the mounting pads. Each bandage is then joined by a temporary adhesive to a support strip containing a pull tab. The continuous sheet and each support strip are sealed together by the temporary adhesive so as to enclose the bandage.

When the tab of a support strip is pulled, the support strip and the adhesive bandage strip are peeled together from the continuous sheet and the mounting pad, leaving the cotton gauze area of the bandage strip exposed. The adhesive bandage strip may then be placed on the desired location and the support strip is peeled away from the bandage strip.

The temporary adhesive joining the bandage strip and the support strip is strong enough to permit the bandage strip and the support strip to be removed together from the mounting pad and the continuous sheet, but also permits easy removal of the support strip after the bandage is affixed to the skin. This is due to the fact that the temporary adhesive joining the adhesive bandage strip to the support strip creates a bond of greater strength than that between the adhesive bandage strip and the nonstick mounting pad, but of lesser strength than the bond between the adhesive bandage strip and a user's skin.

The dispenser itself may be a desktop or wall-mounted refillable container constructed of metal, plastic or paper. The dispenser has an opening or a window to provide access to sterile, individually wrapped adhesive bandage strips affixed to a continuous sheet. The continuous sheet is layered or rolled in the bottom of the dispenser and is fed across the dispenser window and exits either through one end of the dispenser or is attached to a spool. As the bandage strips are used, the sheet may be pulled through or the spool advanced, thus exposing additional bandage strips in the dispenser window.

Thus, it is an object of the present invention to provide an improved dispenser for adhesive-back articles such as adhesive bandage strips.

It is also an object of present invention to provide a device and method allowing the user to apply a common sterile adhesive bandage strip using only one hand in the process of removing the bandage strip from the dispenser and applying it to the desired location.

It is a further object of the invention to provide a convenient dispenser which displays several adhesive bandage strips for immediate use and eliminates the handling of individually wrapped bandage strips and the disposal of the wrappings.

It is a still further object of this invention to provide a method for one-handed application of a bandage strip to its desired location without the bandage strip curling or adhering to itself.

Other objectives, features and advantages of the present invention will become apparent upon reading the following specification, when taken in conjunction with the drawings and the claims.

BRIEF DESCRIPTION OF DRAWINGS

FIG. 1 is a perspective view showing an adhesive bandage strip joined to a support strip with a pull tab.

FIG. 2 is a top perspective view showing the positioning of the adhesive bandage strips and the support strips on the continuous sheet.

FIG. 3 is a perspective view showing the typical application of an adhesive bandage strip with a support strip to a user's skin.

FIG. 4 is an exploded perspective view showing the elements of the dispenser.

FIG. 5 is a side cut away view showing the dispenser packed with a continuous sheet of adhesive bandage strips.

DETAILED DESCRIPTION

FIG. 1 is a perspective view showing an adhesive bandage strip 1 joined to a support sheet 4 with a pull tab 5. The adhesive bandage strip 1 is generally constructed out of plastic, paper or cloth material with an adhesive substance on one side 2 of the strip and a cotton gauze area 3 in the middle of this adhesive side 2 of the strip. A conventional adhesive bandage strip, such as the "Band-Aid®" brand bandage strip, may be used.

The adhesive bandage strip 1 is joined to a support strip 5 by a temporary adhesive. The support strip may be constructed out of paper or plastic material. The temporary adhesive used to join the adhesive bandage strip 1 and the support strip 4 is of the same or lower bonding strength than the adhesive substance used on the adhesive side 2 of the adhesive bandage strip 1. Examples of the temporary adhesive substance include "DryLine™" Temporary Adhesive made by The Gillette Company. The support strip 4 also contains a pull tab 5 for ease of removal, as explained below.

FIG. 2 is a top perspective view showing the positioning of the adhesive bandage strips 1 and the support strips 4 on the continuous sheet 6. The continuous sheet 6 may be constructed out of paper or plastic material. It is of variable length and can be folded accordion-like, as shown, or rolled.

A variable number of sterile, nonstick mounting pads 7 are permanently affixed to the continuous sheet 6. The sterile, nonstick mounting pads 7 are generally constructed out of paper, such as the release liner-type paper manufactured by Rhinelander Paper Company. The adhesive bandage strips 1 are then positioned on the sterile, nonstick mounting pads 7 such that the adhesive side 2 of a bandage strip 1 is in contact with the sterile, nonstick mounting pad 7. Alternatively, the continuous sheet 6 itself can be treated with a nonstick substance such that the adhesive bandage strips 1 may be placed directly on the continuous sheet 6.

A support strip 4 is then joined to each of the adhesive bandage strips 1 as discussed above. The support strip 4 covers the adhesive bandage strip 1 and adheres to that area of the continuous sheet 6 immediately surrounding the adhesive bandage strip 1, such that each adhesive bandage strip 1 is sealed within the support strip 4 and the continuous sheet 1. This enclosure ensures that the adhesive bandage strips 1 remain sterile until use.

In operation, the support strip 4 is grasped via the pull tab 5 such that the adhesive bandage strip 1 and the support strip 4 are peeled together from the sterile, nonstick mounting pad 7 and the continuous strip 6. The temporary adhesive joining the bandage strip 1 and the support strip 4 is of sufficient strength to overcome the bond between the adhesive side 2 of bandage strip 1 and sterile, nonstick mounting pad 7. The adhesive bandage strip 1, supported by support strip 4, is then applied to the desired location on the user's skin.

FIG. 3 is a perspective view showing the typical application of an adhesive bandage strip 1 with a support strip 4 to a user's skin. Once the adhesive bandage strip 1 is applied, the support strip 4 is peeled away from the user and the adhesive bandage strip 1. The temporary adhesive joining the adhesive bandage strip 1 and the support strip 4 is of lesser strength than the bond between the adhesive side 2 of bandage strip 1 and a user's skin. The support strip 4 is then discarded after use.

FIG. 4 is an exploded perspective view showing the elements of dispenser 10. The dispenser 10 consists of a top half 11 defining an access window 12, a bottom half 13, a support ledge 14, a spool 15, and a knob 16. As can be shown, the support ledge 14 is positioned within top half 11 directly underneath access window 12 and is supported by bottom half 13. The bottom half 13 is generally hollow so as to provide space for the packing of the continuous sheet 6. The spool 15 is generally located on one end of the lower half 13 and communicates with knob 16 on the exterior of the dispenser 10.

The dispenser 10 can be manufactured out of metal, plastic or paper. The dispenser 10 may be refillable and may be used on a desktop or mounted to the wall.

FIG. 5 is a side cut away view showing the dispenser 10 packed with a continuous sheet 6 of adhesive bandage strips 1. As can be seen, the continuous sheet 6 is packed accordion-like in the bottom half 12 of dispenser 10. The continuous sheet 6 is fed through and across support ledge 14 such that the adhesive bandage strips 1 are exposed through access window 12. The leading end 8 of continuous sheet 6 is attached to spool 15 such that the continuous sheet 6 can be advanced by rotating knob 16 as the adhesive bandage strips 1 are removed.

In an alterative embodiment, not shown, spool 15 and knob. 16 can be eliminated in favor of an aperture in the upper half 11 of dispenser 10 or between the upper half 11 and lower half 13, such that the leading end 8 of continuous sheet 6 is fed through the opening. The continuous sheet 6 may be pulled through the aperture so as to advance the continuous sheet 6 as the adhesive bandage strips 1 are removed from the access window 12.

While the invention has been disclosed with respect to an adhesive bandage, it will be appreciated that the invention is equally well suited for other types of adhesive-backed articles, e.g., bumper stickers, adhesive-backed name tags, and the like. It is also understood that this description is not meant to be limiting because further modifications may now suggest themselves to those skilled in the art and is intended to cover such modifications as fall within the scope of the following claims.

I claim:

1. A packaged adhesive-backed article, comprising:

an adhesive-backed article having top and bottom surfaces and a first adhesive disposed on at least a portion of said bottom surface;

a backing layer having a top surface, said bottom surface of said adhesive-backed article being removably bonded to said top surface of said backing layer by a first bond formed by said first adhesive; and a support layer having a bottom surface and a second adhesive disposed on at least a portion of said bottom surface, said top surface of said adhesive-backed article being bonded to said bottom surface of said support layer by a second bond formed by said second adhesive, a portion of said bottom surface of said support layer removably bonded to a portion of said backing layer surrounding said adhesive-backed article to enclose said adhesive-backed article in a sterile condition, said second bond being stronger than said first bond such that when said support layer is separated from said backing layer, said adhesive-backed article remains affixed to said support layer, said support layer configured to allow removal of said adhesive-backed article from said backing layer with the use of one hand and to allow the application of said adhesive-backed article to a recipient surface in a sterile condition with the use of one hand, said second bond being weaker than a bond formed between said first adhesive on said bottom surface of said adhesive-backed article and said recipient surface to which it is applied.

2. The packaged adhesive-backed article of claim 1, wherein said adhesive-backed article comprises an adhesive bandage.

3. The packaged adhesive-backed article of claim 2, wherein at least the portions of said backing layer to which said adhesive-backed article is bonded are coated with a release liner to control the strength of the bond between said adhesive-backed article and said backing layer.

4. The packaged adhesive-backed article of claim 3, wherein only said portions of said backing layer to which said adhesive-backed article is bonded are coated with said release liner.

5. The packaged adhesive-backed article of claim 4, wherein said backing layer is anchored to remain in a fixed position while said support layer and said adhesive-backed article are being removed from said backing layer.

6. The packaged adhesive-backed article of claim 4, wherein said backing layer is wider than said support layer.

7. The packaged adhesive-backed article of claim 6, wherein said backing layer is anchored to remain in a fixed position while said support layer and said adhesive-backed article are being removed from said backing layer.

8. A bandage strip dispensing assembly, comprising:

a continuous sheet, said sheet containing one or more removable, individual adhesive bandage strips; a dispenser, said dispenser configured to allow access to at least one of said adhesive bandage strips with the use of one hand;

means for supporting each of said individual adhesive bandage strips while each of said individual adhesive bandage strips is being removed from said dispenser and said continuous sheet with the use of one hand and while being applied to a desired location in a sterile condition with the use of one hand, said dispenser further configured to anchor said continuous sheet in a fixed position while said means for supporting said individual adhesive bandage strips and said individual adhesive bandage strips are being removed from said continuous sheet; and means for removing said means for supporting each of said individual bandage strips with one hand from each of said individual adhesive bandage strips once each of said individual adhesive bandage strips has been applied to said desired location.

9. The bandage strip dispensing assembly of claim 8, wherein said continuous sheet is wider than said means for supporting each of said individual adhesive bandage strips and wherein at least a portion of said backing layer is removably retained by said dispenser.

10. The bandage strip dispensing assembly of claim 8, wherein said continuous sheet containing one or more removable, individual adhesive bandage strips comprises one or more nonstick mounting pads affixed to said continuous sheet, wherein one of said individual adhesive bandage strips is positioned on each of said nonstick mounting pads, forming a first bond therebetween.

11. The bandage strip dispensing assembly of claim 10, wherein said continuous sheet further comprises a plurality of perforations configured to delineate separate continuous sheet segments.

12. The bandage strip dispensing assembly of claim 10, wherein said means for supporting each of said individual adhesive bandage strips while each is being removed from said dispenser and said continuous sheet with the use of one hand and being applied to a respective desired location in a sterile condition with the use of one hand, comprises:

a support strip removably joined by an adhesive substance to, and covering each of, said individual adhesive bandage strips and the portion of said continuous sheet immediately surrounding each of said individual adhesive bandage strips; and a pull tab affixed to each of said support strips, said adhesive substance between each of said support strips and each of said individual adhesive bandage strips forming a second bond, said bond being stronger than said first bond between said individual adhesive bandage strips and said nonstick mounting pads but weaker than a bond formed when each of said individual adhesive bandage strips is affixed to each said respective desired location.

13. The bandage strip dispensing assembly of claim 12, wherein said dispenser comprises:

an upper half defining an access window;

a lower half, said upper half and said lower half being detachably connected;

a support ledge positioned underneath said access window of said upper half and supported by said lower half; and a spool positioned within said upper half and said lower half, and supported by said lower half.

14. The bandage strip dispensing assembly of claim 12, wherein said dispenser comprises:

an upper half defining an access window;

a lower half;

said upper half and said lower half being detachably connected;

a support ledge positioned underneath said access window of said upper half and supported by said lower half; and said upper half and said lower half defining an aperture adjacent to said support ledge.

15. The bandage strip dispensing assembly of claim 10, wherein said continuous sheet is folded.

16. An assemblage of packaged adhesive-backed articles, comprising:

a plurality of adhesive-backed articles, each said adhesive-backed article having top and bottom surfaces and a first adhesive disposed on at least a portion of said bottom surface;

a backing layer having a top surface, said bottom surface of each of said adhesive-backed articles being removably bonded to said top surface of said backing layer by a first bond formed by said first adhesive; and a plurality of discrete support sheets, each support sheet having a bottom surface and a second adhesive disposed on at least a portion of said bottom surface, said top surface of each said adhesive-backed article being removably bonded to a said bottom surface of a respective support sheet by a second bond formed by said second adhesive, said bottom surface of each said support sheet being removably bonded to the portion of said backing layer surrounding a respective adhesive-backed article, said second bond being stronger than said first bond such that when each said support sheet is separated from said backing layer, one of said adhesive-backed articles remains affixed to said support sheet, each said support sheet configured to allow removal of one adhesive-backed article from said backing layer with the use of one hand and to allow the application of said adhesive-backed article to a recipient surface in a sterile condition with the use of one hand, said second bond being weaker than a bond formed between said first adhesive on said bottom surface of one of said adhesive-backed articles and said recipient surface to which it is applied.

17. The assemblage of packaged adhesive-backed articles of claim 16, wherein each of said discrete support sheets further comprises a tab, said tab facilitating removal of said discrete support sheet from said backing layer with one hand, said tab further facilitating the removal of said discrete support sheet from a respective said adhesive-backed article once said adhesive-backed article has been applied to a recipient surface.

18. The assemblage of packaged adhesive-backed articles of claim 16, wherein said backing layer is folded.

19. The assemblage of packaged adhesive-backed articles of claim 16, wherein only said portions of said backing layer to which said adhesive-backed articles are bonded are coated with a release liner.

20. The assemblage of packaged adhesive-backed articles of claim 16, wherein said plurality of support sheets is formed by the perforation of a continuous support layer.

21. The assemblage of packaged adhesive-backed articles of claim 16, wherein said backing layer further comprises a plurality of perforations configured to delineate separate backing sheet segments.

22. The assemblage of packaged adhesive-backed articles of claim 21, wherein said adhesive-backed articles comprise adhesive bandages.

23. The assemblage of packaged adhesive-backed articles of claim 16, wherein at least the portions of said backing layer to which said adhesive-backed articles are bonded are coated with a release liner.

24. The assemblage of packaged adhesive-backed articles of claim 23, wherein said adhesive-backed articles comprise adhesive bandages.

25. The assemblage of packaged adhesive-backed articles of claim 16, wherein said adhesive-backed articles comprise adhesive bandage strips.

26. The assemblage of packaged adhesive-backed articles of claim 25, wherein at least the portions of said backing layer to which said adhesive-backed articles are bonded are coated with a release liner.

27. The assemblage of packaged adhesive-backed articles of claim 25, wherein only said portions of said backing layer to which said adhesive-backed articles are bonded are coated with a release liner.

28. A bandage strip dispensing assembly, comprising:

a continuous sheet;

one or more individual adhesive bandage strips removably mounted to said continuous sheet, said continuous sheet removably anchored in a fixed position;

means for supporting each of said individual adhesive bandage strips while each of said individual adhesive bandage strips is being removed from said continuous sheet with the use of one hand and while being applied to a desired location in a sterile condition with the use of one hand, said continuous sheet anchored in a fixed position to allow the removal of said individual adhesive bandage strips and said means for supporting said individual adhesive bandage strips from said continuous sheet; and means for removing said means for supporting each of said individual bandage strips with one hand from each of said individual adhesive bandage strips once each of said individual adhesive bandage strips has been applied to said desired location.

29. The bandage strip dispensing assembly of claim 28, wherein said continuous sheet further comprises a plurality of perforations configured to delineate separate continuous sheet segments.

30. The bandage strip dispensing assembly of claim 28, wherein said continuous sheet is folded.

* * * * *